(12) United States Patent
Hassan

(10) Patent No.: US 10,416,183 B2
(45) Date of Patent: Sep. 17, 2019

(54) LABORATORY SAMPLE DISTRIBUTION SYSTEM AND LABORATORY AUTOMATION SYSTEM

(71) Applicant: Roche Diagnostics Operations, Inc., Indianapolis, IN (US)

(72) Inventor: Ahmed Hassan, Waiblingen (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 0 days.

(21) Appl. No.: 15/823,746

(22) Filed: Nov. 28, 2017

(65) Prior Publication Data

US 2018/0156835 A1 Jun. 7, 2018

(30) Foreign Application Priority Data

Dec. 1, 2016 (EP) .................................. 16201805

(51) Int. Cl.
*G01N 35/10* (2006.01)
*G01N 35/04* (2006.01)
(Continued)

(52) U.S. Cl.
CPC ......... *G01N 35/1081* (2013.01); *B65G 54/02* (2013.01); *G01N 35/00722* (2013.01);
(Continued)

(58) Field of Classification Search
CPC ......... G01N 35/1081; G01N 35/00722; G01N 35/04; G01N 2035/00752;
(Continued)

(56) References Cited

U.S. PATENT DOCUMENTS 3,273,727 A 9/1966 Rogers et al.
3,653,485 A 4/1972 Donlon
(Continued)

FOREIGN PATENT DOCUMENTS

CN 201045617 Y 4/2008
CN 102109530 A 6/2011
(Continued)

OTHER PUBLICATIONS

European Search Report dated May 23, 2017, in Application No. EP 16201805, 8 pages.

*Primary Examiner* — Nathaniel T Woodward
(74) *Attorney, Agent, or Firm* — Roche Diagnostics Operations, Inc.

(57) ABSTRACT

A laboratory sample distribution system is presented. The system comprises a number of sample container carriers to carry one or more sample containers. Each sample container carrier comprises at least one magnetically active device. The system also comprises a transport plane to support the sample container carriers and a number of electro-magnetic actuators stationary arranged below the transport plane. The electro-magnetic actuators move the sample container carriers on top of the transport plane by applying a magnetic force to the sample container carriers. The system also comprises a rotating device comprising a rotating surface and a rotating drive to cause a rotational movement of the rotating surface. The system also comprises a control device to drive the electro-magnetic actuators, such that a sample container carrier to be rotated moves on the rotating surface, and to control the rotating drive such that a rotation of the sample container carrier is caused.

10 Claims, 2 Drawing Sheets

(51) Int. Cl.
  *B65G 54/02* (2006.01)
  *G01N 35/00* (2006.01)
  *B01L 9/06* (2006.01)

(52) U.S. Cl.
  CPC ............... *G01N 35/04* (2013.01); *B01L 9/06* (2013.01); *G01N 2035/00752* (2013.01); *G01N 2035/0406* (2013.01); *G01N 2035/0477* (2013.01)

(58) Field of Classification Search
  CPC ... G01N 2035/0477; G01N 2035/0406; B65G 54/02; B01L 9/06
  See application file for complete search history.

(56) References Cited

U.S. PATENT DOCUMENTS

| | | |
|---|---|---|
| 3,901,656 A | 8/1975 | Durkos et al. |
| 4,150,666 A | 4/1979 | Brush |
| 4,395,164 A | 7/1983 | Beltrop et al. |
| 4,544,068 A | 10/1985 | Cohen |
| 4,771,237 A | 9/1988 | Daley |
| 5,120,506 A | 6/1992 | Saito et al. |
| 5,295,570 A | 3/1994 | Grecksch et al. |
| 5,309,049 A | 5/1994 | Kawada et al. |
| 5,457,368 A | 10/1995 | Jacobsen et al. |
| 5,523,131 A | 6/1996 | Isaacs et al. |
| 5,530,345 A | 6/1996 | Murari et al. |
| 5,636,548 A | 6/1997 | Dunn et al. |
| 5,641,054 A | 6/1997 | Mori et al. |
| 5,651,941 A | 7/1997 | Stark et al. |
| 5,720,377 A | 2/1998 | Lapeus et al. |
| 5,735,387 A | 4/1998 | Polaniec et al. |
| 5,788,929 A | 8/1998 | Nesti |
| 6,045,319 A | 4/2000 | Uchida et al. |
| 6,062,398 A | 5/2000 | Thalmayr |
| 6,141,602 A | 10/2000 | Igarashi et al. |
| 6,151,535 A | 11/2000 | Ehlers |
| 6,184,596 B1 | 2/2001 | Ohzeki |
| 6,191,507 B1 | 2/2001 | Peltier et al. |
| 6,206,176 B1 | 3/2001 | Blonigan et al. |
| 6,255,614 B1 | 7/2001 | Yamakawa et al. |
| 6,260,360 B1 | 7/2001 | Wheeler |
| 6,279,728 B1 | 8/2001 | Jung et al. |
| 6,293,750 B1 | 9/2001 | Cohen et al. |
| 6,429,016 B1 | 8/2002 | McNeil |
| 6,444,171 B1 | 9/2002 | Sakazume et al. |
| 6,571,934 B1 | 6/2003 | Thompson et al. |
| 7,028,831 B2 | 4/2006 | Veiner |
| 7,078,082 B2 | 7/2006 | Adams |
| 7,122,158 B2 | 10/2006 | Itoh |
| 7,278,532 B2 | 10/2007 | Martin |
| 7,326,565 B2 | 2/2008 | Yokoi et al. |
| 7,425,305 B2 | 9/2008 | Itoh |
| 7,428,957 B2 | 9/2008 | Schaefer |
| 7,578,383 B2 | 8/2009 | Itoh |
| 7,597,187 B2 | 10/2009 | Bausenwein et al. |
| 7,850,914 B2 | 12/2010 | Veiner et al. |
| 7,858,033 B2 | 12/2010 | Itoh |
| 7,875,254 B2 | 1/2011 | Garton et al. |
| 7,939,484 B1 | 5/2011 | Loeffler et al. |
| 8,240,460 B1 | 8/2012 | Bleau et al. |
| 8,281,888 B2 | 10/2012 | Bergmann |
| 8,502,422 B2 | 8/2013 | Lykkegaard |
| 8,796,186 B2 | 8/2014 | Shirazi |
| 8,833,544 B2 | 9/2014 | Stoeckle et al. |
| 8,973,736 B2 | 3/2015 | Johns et al. |
| 9,097,691 B2 | 8/2015 | Onizawa et al. |
| 9,187,268 B2 | 11/2015 | Denninger et al. |
| 9,211,543 B2 | 12/2015 | Ohga et al. |
| 9,239,335 B2 | 1/2016 | Heise et al. |
| 9,423,410 B2 | 8/2016 | Buehr |
| 9,423,411 B2 | 8/2016 | Riether |
| 9,567,167 B2 | 2/2017 | Sinz |
| 9,575,086 B2 | 2/2017 | Heise et al. |
| 9,593,970 B2 | 3/2017 | Sinz |
| 9,598,243 B2 | 3/2017 | Denninger et al. |
| 9,618,525 B2 | 4/2017 | Malinowski et al. |
| 9,658,241 B2 | 5/2017 | Riether et al. |
| 9,664,703 B2 | 5/2017 | Heise et al. |
| 9,791,468 B2 | 10/2017 | Riether et al. |
| 9,952,242 B2 | 4/2018 | Riether |
| 2002/0009391 A1 | 1/2002 | Marquiss et al. |
| 2003/0092185 A1 | 5/2003 | Qureshi et al. |
| 2004/0050836 A1 | 3/2004 | Nesbitt et al. |
| 2004/0084531 A1 | 5/2004 | Itoh |
| 2005/0061622 A1 | 3/2005 | Martin |
| 2005/0109580 A1 | 5/2005 | Thompson |
| 2005/0194333 A1 | 9/2005 | Veiner et al. |
| 2005/0196320 A1 | 9/2005 | Veiner et al. |
| 2005/0226770 A1 | 10/2005 | Allen et al. |
| 2005/0242963 A1 | 11/2005 | Oldham |
| 2005/0247790 A1 | 11/2005 | Itoh |
| 2005/0260101 A1 | 11/2005 | Nauck et al. |
| 2005/0271555 A1 | 12/2005 | Itoh |
| 2006/0000296 A1 | 1/2006 | Salter |
| 2006/0047303 A1 | 3/2006 | Ortiz et al. |
| 2006/0219524 A1 | 10/2006 | Kelly |
| 2007/0116611 A1 | 5/2007 | DeMarco |
| 2007/0210090 A1 | 9/2007 | Sixt et al. |
| 2007/0248496 A1 | 10/2007 | Bondioli et al. |
| 2007/0276558 A1 | 11/2007 | Kim |
| 2008/0012511 A1 | 1/2008 | Ono |
| 2008/0029368 A1 | 2/2008 | Komori |
| 2008/0056328 A1 | 3/2008 | Rund et al. |
| 2008/0131961 A1 | 6/2008 | Crees et al. |
| 2009/0004732 A1 | 1/2009 | LaBarre et al. |
| 2009/0022625 A1 | 1/2009 | Lee et al. |
| 2009/0081771 A1 | 3/2009 | Breidford et al. |
| 2009/0128139 A1 | 5/2009 | Drenth et al. |
| 2009/0142844 A1 | 6/2009 | Le Comte |
| 2009/0180931 A1 | 7/2009 | Silbert et al. |
| 2009/0322486 A1 | 12/2009 | Gerstel |
| 2010/0000250 A1 | 1/2010 | Sixt |
| 2010/0152895 A1 | 6/2010 | Dai |
| 2010/0175943 A1 | 7/2010 | Bergmann |
| 2010/0186618 A1 | 7/2010 | King et al. |
| 2010/0255529 A1 | 10/2010 | Cocola et al. |
| 2010/0300831 A1 | 12/2010 | Pedrazzini |
| 2010/0312379 A1 | 12/2010 | Pedrazzini |
| 2011/0050213 A1 | 3/2011 | Furukawa |
| 2011/0124038 A1 | 5/2011 | Bishop et al. |
| 2011/0172128 A1 | 7/2011 | Davies et al. |
| 2011/0186406 A1 | 8/2011 | Kraus et al. |
| 2011/0287447 A1 | 11/2011 | Norderhaug et al. |
| 2012/0037696 A1 | 2/2012 | Lavi |
| 2012/0129673 A1 | 5/2012 | Fukugaki et al. |
| 2012/0178170 A1 | 7/2012 | Van Praet |
| 2012/0211645 A1 | 8/2012 | Tullo et al. |
| 2012/0275885 A1 | 11/2012 | Furrer et al. |
| 2012/0282683 A1 | 11/2012 | Mototsu |
| 2012/0295358 A1 | 11/2012 | Ariff et al. |
| 2012/0310401 A1 | 12/2012 | Shah |
| 2013/0034410 A1 | 2/2013 | Heise et al. |
| 2013/0153677 A1 | 6/2013 | Leen et al. |
| 2013/0180824 A1 | 7/2013 | Kleinikkink et al. |
| 2013/0263622 A1 | 10/2013 | Mullen |
| 2013/0322992 A1 | 12/2013 | Pedrazzini |
| 2014/0170023 A1 | 6/2014 | Saito et al. |
| 2014/0234949 A1 | 8/2014 | Wasson et al. |
| 2014/0374480 A1* | 12/2014 | Pollack .................. G01N 35/04 235/440 |
| 2015/0014125 A1 | 1/2015 | Hecht |
| 2015/0166265 A1 | 6/2015 | Pollack et al. |
| 2015/0241457 A1 | 8/2015 | Miller |
| 2015/0273468 A1 | 10/2015 | Croquette et al. |
| 2015/0273691 A1 | 10/2015 | Pollack |
| 2015/0276775 A1 | 10/2015 | Mellars et al. |
| 2015/0276776 A1 | 10/2015 | Riether |
| 2015/0276778 A1 | 10/2015 | Riether et al. |
| 2015/0276782 A1 | 10/2015 | Riether |
| 2016/0003859 A1 | 1/2016 | Wenczel et al. |
| 2016/0025756 A1 | 1/2016 | Pollack et al. |
| 2016/0054341 A1 | 2/2016 | Edelmann |

(56) References Cited

U.S. PATENT DOCUMENTS

| | | |
|---|---|---|
| 2016/0077120 A1 | 3/2016 | Riether |
| 2016/0229565 A1 | 8/2016 | Margner |
| 2016/0274137 A1 | 9/2016 | Baer |
| 2016/0282378 A1 | 9/2016 | Malinowski et al. |
| 2016/0341750 A1 | 11/2016 | Sinz et al. |
| 2016/0341751 A1 | 11/2016 | Huber et al. |
| 2017/0059599 A1 | 3/2017 | Riether |
| 2017/0096307 A1 | 4/2017 | Mahmudimanesh et al. |
| 2017/0097372 A1 | 4/2017 | Heise et al. |
| 2017/0101277 A1 | 4/2017 | Malinowski |
| 2017/0108522 A1 | 4/2017 | Baer |
| 2017/0131307 A1 | 5/2017 | Pedain |
| 2017/0131309 A1 | 5/2017 | Pedain |
| 2017/0131310 A1 | 5/2017 | Volz et al. |
| 2017/0138971 A1 | 5/2017 | Heise et al. |
| 2017/0160299 A1 | 6/2017 | Schneider et al. |
| 2017/0168079 A1 | 6/2017 | Sinz |
| 2017/0174448 A1 | 6/2017 | Sinz |
| 2017/0184622 A1 | 6/2017 | Sinz et al. |
| 2017/0248623 A1 | 8/2017 | Kaeppeli et al. |
| 2017/0248624 A1 | 8/2017 | Kaeppeli et al. |
| 2017/0363608 A1 | 12/2017 | Sinz |
| 2018/0067141 A1 | 3/2018 | Mahmudimanesh et al. |
| 2018/0074087 A1 | 3/2018 | Heise et al. |
| 2018/0106821 A1 | 4/2018 | Vollenweider et al. |
| 2018/0128848 A1 | 5/2018 | Schneider et al. |
| 2018/0188280 A1 | 7/2018 | Malinowski |
| 2018/0210000 A1 | 7/2018 | Van Mierlo |
| 2018/0210001 A1 | 7/2018 | Reza |
| 2018/0217174 A1 | 8/2018 | Malinowski |
| 2018/0217176 A1 | 8/2018 | Sinz et al. |
| 2018/0224476 A1 | 8/2018 | Birrer et al. |
| 2018/0348244 A1 | 12/2018 | Ren |
| 2019/0018027 A1 | 1/2019 | Hoehnel |
| 2019/0086433 A1 | 3/2019 | Hermann et al. |

FOREIGN PATENT DOCUMENTS

| | | | |
|---|---|---|---|
| DE | 3909786 A1 | 9/1990 | |
| DE | 102012000665 A1 | 8/2012 | |
| DE | 102011090044 A1 | 7/2013 | |
| EP | 0601213 A1 | 10/1992 | |
| EP | 0775650 A1 | 5/1997 | |
| EP | 0916406 A2 | 5/1999 | |
| EP | 1122194 A1 | 8/2001 | |
| EP | 1524525 A1 | 4/2005 | |
| EP | 2119643 A1 | 11/2009 | |
| EP | 2148117 A1 | 1/2010 | |
| EP | 2327646 A1 | 6/2011 | |
| EP | 2447701 A2 | 5/2012 | |
| EP | 2500871 A1 | 9/2012 | |
| EP | 2502675 B1 | 2/2014 | |
| EP | 2887071 A1 | 6/2015 | |
| EP | 3064947 A1 | 9/2016 | |
| EP | 3070479 A1 * | 9/2016 | ............ G01N 35/04 |
| GB | 2165515 A | 4/1986 | |
| JP | S56-147209 A | 11/1981 | |
| JP | 60-223481 A | 11/1985 | |
| JP | 61-081323 A | 4/1986 | |
| JP | S61-069604 A | 4/1986 | |
| JP | S61-094925 A | 5/1986 | |
| JP | S61-174031 A | 8/1986 | |
| JP | S61-217434 A | 9/1986 | |
| JP | S62-100161 A | 5/1987 | |
| JP | S63-31918 A | 2/1988 | |
| JP | S63-48169 A | 2/1988 | |
| JP | S63-82433 U | 5/1988 | |
| JP | S63-290101 A | 11/1988 | |
| JP | 1148966 A | 6/1989 | |
| JP | H01-266860 A | 10/1989 | |
| JP | H02-87903 A | 3/1990 | |
| JP | 03-112393 A | 5/1991 | |
| JP | 03-192013 A | 8/1991 | |
| JP | H03-38704 Y2 | 8/1991 | |
| JP | H04-127063 A | 4/1992 | |
| JP | H05-69350 A | 3/1993 | |
| JP | H05-142232 A | 6/1993 | |
| JP | H05-180847 A | 7/1993 | |
| JP | 06-26808 A | 2/1994 | |
| JP | H06-148198 A | 5/1994 | |
| JP | 06-156730 A | 6/1994 | |
| JP | 06-211306 A | 8/1994 | |
| JP | 07-228345 A | 8/1995 | |
| JP | 07-236838 A | 9/1995 | |
| JP | H07-301637 A | 11/1995 | |
| JP | H09-17848 A | 1/1997 | |
| JP | H11-083865 A | 3/1999 | |
| JP | H11-264828 A | 9/1999 | |
| JP | H11-304812 A | 11/1999 | |
| JP | H11-326336 A | 11/1999 | |
| JP | 2000-105243 A | 4/2000 | |
| JP | 2000-105246 A | 4/2000 | |
| JP | 2001-124786 A | 5/2001 | |
| JP | 2001-240245 A | 9/2001 | |
| JP | 2005-001055 A | 1/2005 | |
| JP | 2005-249740 A | 9/2005 | |
| JP | 2006-106008 A | 4/2006 | |
| JP | 2007-309675 A | 11/2007 | |
| JP | 2007-314262 A | 12/2007 | |
| JP | 2007-322289 A | 12/2007 | |
| JP | 2009-036643 A | 2/2009 | |
| JP | 2009-062188 A | 3/2009 | |
| JP | 2009-145188 A | 7/2009 | |
| JP | 2009-300402 A | 12/2009 | |
| JP | 2010-243310 A | 10/2010 | |
| JP | 2013-172009 A | 2/2013 | |
| JP | 2013-190400 A | 9/2013 | |
| SU | S85591 A1 | 9/1979 | |
| WO | 1996/036437 A1 | 11/1996 | |
| WO | 2003/042048 A3 | 5/2003 | |
| WO | 2007/024540 A1 | 3/2007 | |
| WO | 2008/133708 A1 | 11/2008 | |
| WO | 2009/002358 A1 | 12/2008 | |
| WO | 2010/042722 A1 | 4/2010 | |
| WO | 2012/170636 A1 | 7/2010 | |
| WO | 2010/087303 A1 | 8/2010 | |
| WO | 2010/129715 A1 | 11/2010 | |
| WO | 2012/158520 A1 | 11/2012 | |
| WO | 2012/158541 A1 | 11/2012 | |
| WO | 2013/152089 A1 | 10/2013 | |
| WO | 2013/169778 A1 | 11/2013 | |
| WO | 2013/177163 A1 | 11/2013 | |
| WO | 2014/059134 A1 | 4/2014 | |
| WO | 2014/071214 A1 | 5/2014 | |

* cited by examiner

LABORATORY SAMPLE DISTRIBUTION SYSTEM AND LABORATORY AUTOMATION SYSTEM

CROSS-REFERENCE TO RELATED APPLICATIONS

This application is based on and claims priority to EP 16201805.5, filed Dec. 1, 2016, which is hereby incorporated by reference.

BACKGROUND

The present disclosure relates to a laboratory sample distribution system and a laboratory automation system.

Known laboratory sample distribution systems are typically used in laboratory automation systems in order to transport samples contained in sample containers between different laboratory stations. A typical laboratory sample distribution system provides for a high throughput and for reliable operation.

Sample containers distributed by a laboratory sample distribution system may contain barcodes or other identification tags in order to identify a sample contained in the sample container. Such identification tags may be read out by optical recognition devices, for example by barcode readers or cameras.

However, it has been found that reading such identification tags is complicated in certain situations, because the identification tags usually do not span a whole circumference of the sample container. As the sample containers can typically rotate freely on a transport plane of a laboratory sample distribution system, it is possible that a reading device is not able to identify a sufficient portion of the identification tag when a sample container is placed at a certain position in order to read the identification tag.

Therefore, there is a need for a laboratory sample distribution system and a laboratory automation system for identifying a sufficient portion of the identification tag of the sample container.

SUMMARY

According to the present disclosure, a laboratory sample distribution system. The laboratory sample distribution system can comprise a number of sample container carriers adapted to carry one or more sample containers. Each sample container carrier can comprise at least one magnetically active device. The laboratory sample distribution system can also comprise a transport plane adapted to support the sample container carriers and a number of electro-magnetic actuators stationary arranged below the transport plane. The electro-magnetic actuators can be adapted to move the sample container carriers on top of the transport plane by applying a magnetic force to the sample container carriers and a rotating device comprising a rotating surface and a rotating drive adapted to cause a rotational movement of the rotating surface. The laboratory sample distribution system can also comprise a control device configured to drive the electro-magnetic actuators such that a sample container carrier to be rotated moves on the rotating surface and configured to control the rotating drive such that a rotation of the sample container carrier is caused.

Accordingly, it is a feature of the embodiments of the present disclosure to provide a laboratory sample distribution system and a laboratory automation system for identifying a sufficient portion of the identification tag of the sample container. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
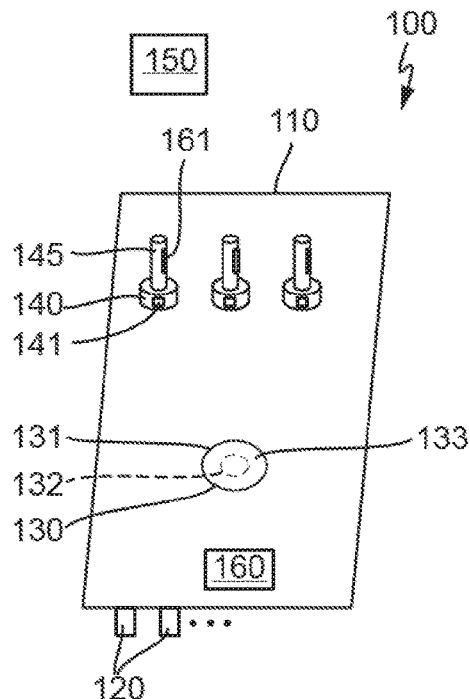
FIG. 1 illustrates schematically a laboratory sample distribution system comprising a rotary plate according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A laboratory sample distribution system can comprise a number of sample container carriers. The number of sample container carriers may e.g. be a number in the range of 1 up to 1,000,000. The sample container carriers can be adapted to carry and/or hold and/or store one or more sample containers. The sample container can typically be designed as a tube made of glass or transparent plastic and typically can have an opening at an upper end. The laboratory sample container may be used to contain, store and transport the laboratory sample such as a blood sample, (blood) serum or plasma sample, a urine sample, separation gel, cruor (blood cells) or a chemical sample. The sample container may be rotationally symmetric.

Each sample container carrier can comprise at least one magnetically active device. The magnetically active device may be a permanent magnet or an electromagnet.

The laboratory sample distribution system can further comprise a transport plane adapted to support or carry the sample container carriers. The transport plane may be a planar plane and the sample container carriers can be placed on top of the transport plane.

The laboratory sample distribution system can further comprise a number of electro-magnetic actuators. The number of electro-magnetic actuators may e.g. be a number in the range of 1 up to 1,000,000.

The electro-magnetic actuators can be stationary arranged below the transport plane, e.g. in rows and columns forming a grid. The electro-magnetic actuators may be coils having a ferromagnetic core. The coils may be adapted to generate a magnetic field. The magnetic field generated by the electro-magnetic actuators may penetrate the transport plane. The magnetic field may interact with the magnetic field of the magnetically active devices of the sample container carriers. The magnetic force applied on the sample container carriers may be a result of this field interaction. Due to the magnetic force, the sample container carriers may slide and/or move over the transport plane. Thus, the electro-magnetic actuators can be adapted to move the sample container carriers on top of the transport plane by applying a magnetic force to the magnetically active devices of the sample container carriers.

The laboratory sample distribution system further comprises a rotating device. The rotating device can comprise a rotating surface. The rotating surface may be a circular surface. The rotating surface may be smaller in its dimensions compared to the dimensions of the transport plane. The rotating surface may be embodied as a specific side, e.g. an upper side, of a rotary element. The rotary element may be rotatably mounted. The rotating device can further comprise a rotating drive adapted to cause a rotational movement of the rotating surface. The rotating drive may be an electric motor or a pneumatic motor. Additionally or alternatively, the electro-magnetic actuators arranged below the transport plane may form the rotating drive.

The laboratory sample distribution system can further comprise a control device, e.g. in form of a Personal Computer (PC) or a microprocessor based control device. The control device can be configured to drive the electro-magnetic actuators. Each sample container carrier may move along a path in response to the driven electro-magnetic actuators. The path of the sample container carriers may be individual paths. The control device can be configured to drive the electro-magnetic actuators such that a sample container carrier to be rotated can move onto the rotating surface. The control device can be further configured to control the rotating drive such that a rotation of the sample container carrier can be caused.

The rotating surface may be larger in its dimensions compared to a footprint of the sample container carrier to be rotated. The rotating surface may be adapted to support or carry the sample container carrier to be rotated. The sample container carrier to be rotated may be placed above or on top of the rotating surface. When placed on the rotating surface, the sample container carrier can rotate together with the carried sample container.

In one embodiment, a (vertical) level of the rotating surface and a level of the transport plane can be identical. The level may be a height having the identical reference point. The identical level of the rotating surface and of the transport plane may prevent tilting of the sample container carrier when the sample container carrier to be rotated moves onto the rotating surface.

In one embodiment, the rotating device can comprise a rotary plate. The rotary plate may be a circular cylinder. An upper side of the rotary plate may form the rotating surface. The upper side may be a facing surface of the rotary plate. The rotating drive can be adapted to cause a rotational movement of the rotary plate. The rotational movement may be caused by a force generated by the rotating drive and applied to the rotary plate. The force may be applied to the rotary plate via a positive connection or a friction-type connection.

In one embodiment, the transport plane can comprise a recess. The recess may have a circular shape. The rotary plate may be arranged inside the recess. The rotary plate may be placed in a rotatable manner inside the recess. Elements defining the recess and the transport plane may be one piece.

In one embodiment, the rotary plate can comprise a magnetically active device having anisotropic magnetic properties such as, for example, an anisotropic magnetic field. A rotating force can be generated by an externally generated magnetic field interacting with a magnetic field of the magnetically active device located in the rotary plate. The magnetically active device located in the rotary plate may be embodied as a permanent magnet, e.g. a bar magnet, or ferromagnetic material.

In one embodiment, the electro-magnetic actuators can comprise respective ferromagnetic cores. The ferromagnetic cores may be embodied as circular cylinders of ferromagnetic material. At least one of the ferromagnetic cores can be arranged vertically movable between an upper vertical position and a lower vertical position. In the lower vertical position, the vertically movable ferromagnetic core may be positioned below the transport plane. In the upper vertical position, a top surface of the vertically moveable ferromagnetic core can contact a bottom surface of the sample container carrier placed above the vertically moveable ferromagnetic core. In the lower vertical position, the top surface of the vertically moveable ferromagnetic core typically does not contact the bottom surface of the sample container carrier. The top surface of the vertically moveable ferromagnetic core can form the rotating surface. The top surface may be an upper side of the vertically moveable ferromagnetic core having a shape in form of a circular cylinder.

The rotating drive can be adapted to cause a rotational movement of the vertically moveable ferromagnetic core. The rotating drive may be functionally coupled to the vertically moveable ferromagnetic core. The rotating drive may apply a force to the vertically moveable ferromagnetic core, wherein the force may cause a rotation of the vertically moveable ferromagnetic core.

In one embodiment, the magnetically active device of a sample container carrier placed above the vertically moveable ferromagnetic core and/or the rotating drive and/or the electro-magnetic actuators can be adapted to move the vertically moveable ferromagnetic core from the upper vertical position to the lower vertical position and/or can be adapted to move the vertically moveable ferromagnetic core from the lower vertical position to the upper vertical position. The movement of the vertically moveable ferromagnetic core may be caused by a force originating from an interaction between a magnetic field and the ferromagnetic material of the ferromagnetic core. The control device may be adapted to control and/or initiate the movement of the vertically moveable ferromagnetic core.

In one embodiment, the rotating surface and a surface of the sample container carrier placed on the rotating surface can form a positive connection or a friction-type connection. The positive connection or friction-type connection may prevent slipping of the sample container carrier at the beginning and/or ending of the rotational movement of the sample container carrier.

In one embodiment, the laboratory sample distribution system can further comprise a barcode scanning unit. The barcode scanning unit can be adapted to scan a barcode label placed on a sample container held by the sample container carrier to be rotated. The control device can be adapted to cause a rotational movement of the rotating surface and consequently of the sample container carrier placed on the rotating surface holding the sample container having the barcode label to be scanned, such that the barcode label can be readable by the barcode scanning unit. The rotating surface may rotate the sample container carrier to be rotated. The barcode scanning unit may be adapted to scan the barcode label during the rotational movement of the sample container carrier. The barcode may determine a destination of the sample container carrier to be transported and/or may comprise information concerning the sample contained in the sample container.

The laboratory automation system can comprises the laboratory sample distribution system described above. The laboratory automation system can further comprise a number of laboratory stations. The number of laboratory stations may e.g. be a number in the range from 1 to 100. The laboratory stations may be e.g. pre-analytical, analytical and/or post-analytical stations.

Pre-analytical stations may be adapted to perform any kind of pre-processing of samples and/or laboratory sample containers.

Analytical stations may be adapted to use a sample or part of the sample and/or a reagent to generate a measuring signal, the measuring signal indicating if and in which concentration an analyte exists.

Post-analytical stations may be adapted to perform any kind of post-processing of samples and/or sample containers.

The pre-analytical, analytical and/or post-analytical stations may comprise at least one of a decapping station, a recapping station, an aliquot station, a centrifugation station, an archiving station, a pipetting station, a sorting station, a tube type identification station, a sample quality determining station, an add-on buffer station, a liquid level detection station, and a sealing/desealing station.

The laboratory sample distribution system can be adapted to distribute the sample containers between the laboratory stations. The laboratory sample distribution system may be adapted to distribute the sample containers between the laboratory stations in response to the scanned barcode labels.

Referring initially to FIG. 1, FIG. 1 schematically depicts a laboratory sample distribution system 100 comprising a number of sample container carriers 140. For the purpose of explanation, only three sample container carriers 140 are shown as representatives for the number of sample container carriers 140. The number of sample container carriers 140 may e.g. be in the range of 10 to 10000. Each sample container carriers 140 can comprise a magnetically active device 141 in the form of a permanent magnet. Moreover, each sample container carrier 140 can hold a sample container 145. A barcode label 161 can be placed on each sample container 145.

The sample container carriers 140 can be placed on a flat transport plane 110 being part of the laboratory sample distribution system 100. The sample container carriers 140 can be adapted to slide and/or move on/over the transport plane 110. Further, a number, or plurality, of electro-magnetic actuators 120 are stationary can be arranged below the transport plane 110. The electro-magnetic actuators 120 can be adapted to generate a magnetic field which can cause a magnetic force on the permanent magnets 141 of the sample container carriers 140. The sample container carriers 140 can move/slide on/over the transport plane 110 as a result of the magnetic force.

The generation of the magnetic field and, therefore, the generation of the magnetic force can be controlled by a control device 150. The control device 150 can be configured to drive the electro-magnetic actuators 120 such that each sample container carrier 140 can slide on an individual path, wherein the path can be planned and/or controlled by the control device 150.

The sample distribution system 100 can further comprise a barcode scanning unit 160. The barcode scanning unit 160 can be adapted to scan the barcode label 161 placed on a respective sample container 145. In order to scan the barcode label 161, the control device 150 can drive the electro-magnetic actuators 120 such that the sample container carrier 140 comprising the sample container 145 having the barcode label 161 to be scanned slides on a rotary plate 133 of a rotating device 130. The rotary plate 133 and the transport plane 110 can have an identical level for preventing that the sample container carrier 140 tilts when sliding from the transport plane 110 on the rotary plate 133.

When the sample container carrier 140 is placed on the rotating surface 131, the control device 150 can control the rotating drive 132 to rotate the sample container carrier 140. The barcode scanning unit 160 can repeatedly try to read the barcode label 161 during the rotation of the sample container carrier 140. When the barcode label 161 is successfully read, the barcode scanning unit 160 can transmit the read barcode to the control device 150 and the control device 150 can stop rotating the rotating surface 131. Then, the control device 150 can drive the electro-magnetic actuators 120 such that the sample container carrier 140 can move off the rotary plate 133.

Figure 2:
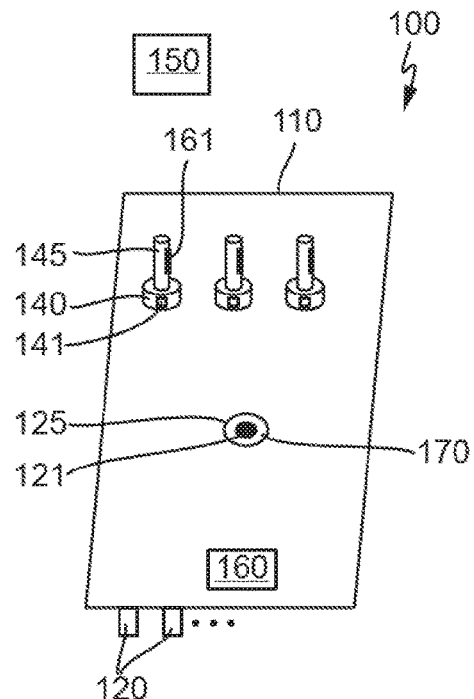
FIG. 2 illustrates schematically a laboratory sample distribution system comprising electro-magnetic actuators having a vertically moveable ferromagnetic core according to an embodiment of the present disclosure.

FIG. 2 shows a further embodiment of a laboratory sample distribution system 100. The laboratory sample distribution system 100 can comprise a transport plane 110 having a cylindrical through hole 125. The through hole 125 can be concentrically arranged with respect to a circular cylindrical vertically moveable ferromagnetic core 121 of an electro-magnetic actuator 120. The through hole 125 can have a diameter that is smaller than a diameter of a respective stand of the sample container carriers 140 and, thus, the sample container carriers 140 can slide and/or move over the opening 125. However, the through hole 125 can have a diameter that is larger than a diameter of the vertically moveable ferromagnetic core 121 and, thus, the vertically moveable ferromagnetic core 121 can penetrate through the transport plane 110.

Figure 3:
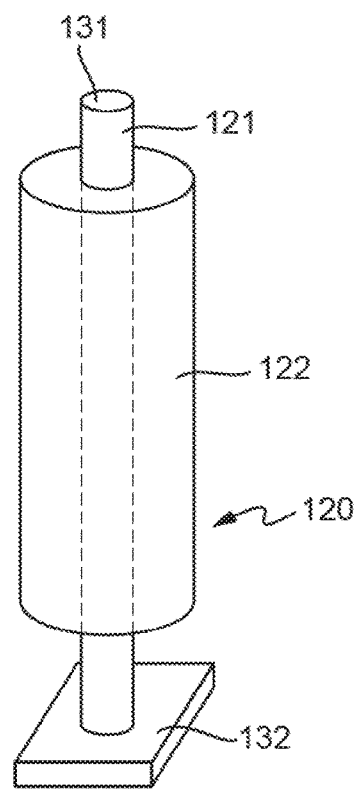
FIG. 3 illustrates schematically an electro-magnetic actuator of FIG. 2 comprising a vertically moveable ferromagnetic core in more detail according to an embodiment of the present disclosure.

FIG. 3 shows the electro-magnetic actuator 120 arranged under the through hole 125 in FIG. 2 in more detail. The electro-magnetic actuator 120 can comprise the vertically moveable ferromagnetic core 121 and a coil 122. The vertically moveable ferromagnetic core 121 can be surrounded by the coil 122. The coil 122 can serve to radially fix the ferromagnetic core 121. The front side or upper side of the vertically moveable ferromagnetic core 121 can form the rotating surface 131.

The vertically moveable ferromagnetic core 121 can be functionally coupled to the rotating drive 132, such that the rotating drive 132 may cause a rotation of the ferromagnetic core 121.

The magnetically active device 141 of a sample container carrier 140 placed above the vertically moveable ferromagnetic core can cause a movement of the vertically moveable ferromagnetic core 121 from a lower vertical position to an upper vertical position. When activated, the coil 122 assigned to the vertically moveable ferromagnetic core 121 can cause a movement of the vertically moveable ferromagnetic core 121 from the upper vertical position back to the lower vertical position, such that the vertically moveable ferromagnetic core 121 may transition between its lower and upper vertical position when necessary.

In the lower vertical position, the rotating surface 131 can be located below the transport plane 110. In the upper vertical position, the rotating surface 131 can pass the opening 125 and contact the bottom of the sample container carrier 140 placed above.

A seal 170 may be located between the through hole 125 and the vertically moveable ferromagnetic core 121. The seal 170 can prevent substances from passing the gap between the transport plane 110 and the moveable ferromagnetic core 121. The seal 170 may e.g. be a gap seal, labyrinth seal or profiles interlocking each other.

In order to scan the barcode label 161, in a first step, the vertically moveable ferromagnetic core 121 can be in the lower vertical position and the control device 150 can drive the electro-magnetic actuators 120 such that the sample container carrier 140 carrying the sample container 145 having the barcode label 161 to be scanned slides above the through hole 125.

The magnetically active device 141 of the sample container carrier 140 can cause the vertical movement of the vertically moveable ferromagnetic core 121 to its upper vertical position.

In the upper vertical position, the vertically moveable ferromagnetic core 121 can contact a bottom surface of the sample container carrier 140 like a friction clutch.

The control device 150 can then initiate a rotational movement of the vertically moveable ferromagnetic core 121 by controlling the rotating drive 132.

The barcode scanning unit 160 can then read the barcode label 161 during the rotational movement of the vertically moveable ferromagnetic core 121. When the barcode label 161 is successfully read, the barcode scanning unit 160 can transmit the read barcode to the control device 150. The control device 150 can be adapted to control the rotating drive 132 such that the rotational movement of the vertically moveable ferromagnetic core 121 can stop after the barcode label has been successfully read.

Then, the control device 150 can initiate the movement of the vertically moveable ferromagnetic core 121 back to its lower vertical position.

Further, the control device 150 can drive the electro-magnetic actuators 120 such that the sample container carrier 140 can move off the through hole 125.

Figure 4:
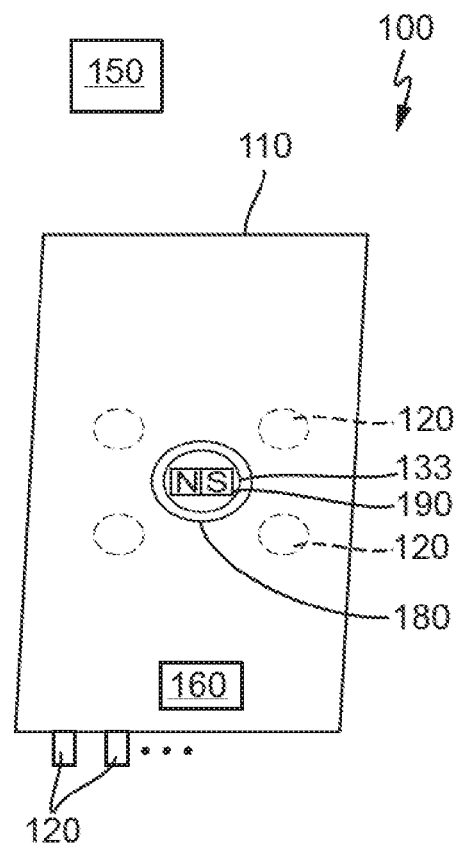
FIG. 4 illustrates schematically depicts a laboratory sample distribution system according to another embodiment of the present disclosure.

Another embodiment of a laboratory sample distribution system 100 is depicted in FIG. 4. The laboratory sample distribution system 100 can comprise a transport plane 110 having a recess 180. The rotary plate 133 can be rotatably inserted into the recess 180. The rotary plate 133 can comprise a magnetically active device 190 in the form of a bar magnet having an anisotropic magnetic field. The bar magnet can extend in a horizontal direction, i.e. parallel to the transport plane 110.

The rotary plate 133 can be rotated by a magnetic force arising from an interaction between the magnetic field of the magnetically active device 190 and the magnetic field of the electro-magnetic actuators 120. The rotary plate 133 including the magnetically active device 190 can form a rotor of an electric motor. The electro-magnetic actuators 120 can form a stator of the electric motor. The electro-magnetic actuators 120 can be controlled such that a rotating magnetic field can be caused, wherein the rotor follows this rotating magnetic field. In other words, the electro-magnetic actuators 120 and the rotary plate 133 can form a synchronous motor.

The rotary plate 133 may contact the bottom surface of the sample container carrier 140 like a friction clutch.

In order to scan the barcode label 161 by the barcode scanning unit 160, the control device 150 can drive the electro-magnetic actuators 120 such that the sample container carrier 140 comprising the sample container 145 having the barcode label 161 to be scanned can slide on the rotary plate 133. Then, the control device 150 can drive the electro-magnetic actuators 120 such that the rotary plate 133 can rotate. The barcode scanning unit 160 can then scan the barcode label 161 during the rotational movement of the rotating device 130, as already discussed with respect to FIGS. 1 to 3.

Figure 5:
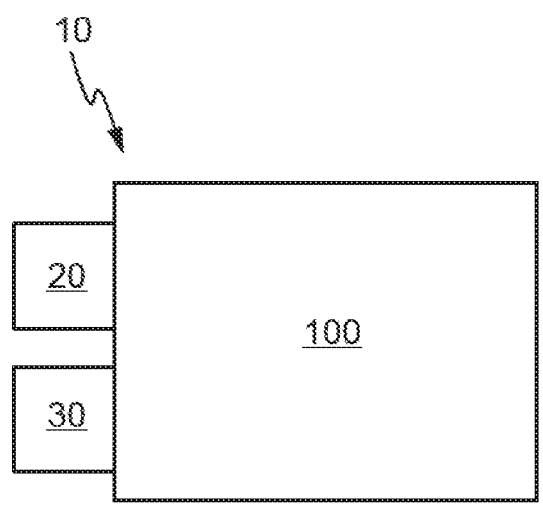
FIG. 5 illustrates schematically a laboratory automation system comprising a sample distribution system according to an embodiment of the present disclosure.

FIG. 5 schematically depicts a laboratory automation system 10 comprising two laboratory stations 20 and 30. The laboratory stations 20 and 30 can process a sample comprised in a sample container 145. For example, the laboratory station 20 can perform a urinalysis and the laboratory station 30 can perform a blood analysis. The laboratory automation system 10 can further comprise a sample distribution system 100 as e.g. be depicted in FIGS. 1 to 4.

The sample distribution system 100 can be adapted to distribute the sample containers 145 between the laboratory stations 20 and 30. The distribution between the laboratory stations 20 and 30 may be done in response to a scanned barcode label 161 placed on the sample container 145. The distribution may be controlled by the control device 150.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A laboratory sample distribution system, the laboratory sample distribution system comprising:
   a number of sample container carriers adapted to carry one or more sample containers, each sample container carrier comprising at least one magnetically active device;
   a transport plane adapted to support the sample container carriers;
   a number of electro-magnetic actuators stationarily arranged below the transport plane, the electro-magnetic actuators adapted to move the sample container carriers on top of the transport plane by applying a magnetic force to the sample container carriers;
   a rotating device comprising
      a rotating surface, and
      a rotating drive adapted to cause a rotational movement of the rotating surface; and
   a control device configured to drive the electro-magnetic actuators such that a sample container carrier to be rotated moves on the rotating surface and is configured to control the rotating drive such that a rotation of the sample container carrier is caused.

2. The laboratory sample distribution system according to claim 1, wherein a level of the rotating surface and a level of the transport plane are identical.

3. The laboratory sample distribution system according to claim 1, wherein the rotating device comprises a rotary plate, wherein a side of the rotary plate forms the rotating surface, and wherein the rotating drive is adapted to cause a rotational movement of the rotary plate.

4. The laboratory sample distribution system according to claim 3, wherein the transport plane comprises a recess and wherein the rotary plate is arranged in the recess.

5. The laboratory sample distribution system according to claim 3, wherein the rotary plate comprises a magnetically active device having anisotropic magnetic properties.

6. The laboratory sample distribution system according to claim 1, wherein the electro-magnetic actuators comprise ferromagnetic cores, wherein at least one of the ferromagnetic cores is vertically movable between an upper vertical position and a lower vertical position, wherein in the upper vertical position a top surface of the vertically moveable ferromagnetic core contacts the sample container carrier placed above the vertically moveable ferromagnetic core, wherein the top surface of the vertically moveable ferromagnetic core forms the rotating surface, and wherein the rotating drive is adapted cause a rotational movement of the vertically moveable ferromagnetic core.

7. The laboratory sample distribution system according to claim 6, wherein the magnetically active device of a sample container carrier placed above the vertically moveable ferromagnetic core and/or the rotating drive and/or an electromagnetic actuator is/are adapted to move the vertically moveable ferromagnetic core from the upper vertical position to the lower vertical position and/or is/are adapted to move the vertically moveable ferromagnetic core from the lower vertical position to the upper vertical position.

8. The laboratory sample distribution system according to claim 1, wherein the rotating surface and a surface of the sample container carrier placed on the rotating surface form a positive connection or a friction-type connection.

9. The laboratory sample distribution system according to claim 1, further comprises,
a barcode scanning unit adapted to scan a barcode label placed on a sample container held by the sample container carrier to be rotated, wherein the control device is adapted to cause a rotational movement of the rotating surface such that the barcode label is readable by the barcode scanning unit.

10. A laboratory automation system, the laboratory automation system comprising:
a number of laboratory stations; and
a laboratory sample distribution system according to claim 1, wherein the laboratory sample distribution system is adapted to distribute the sample containers between the laboratory stations.

* * * * *